(12) United States Patent
Rozzell et al.

(10) Patent No.: US 7,156,884 B2
(45) Date of Patent: Jan. 2, 2007

(54) COMPOSITIONS AND METHODS FOR DYEING KERATINOUS FIBERS

(75) Inventors: David Rozzell, Burbank, CA (US); Juergen Allwohn, Burgschwalbach (DE); Laurent Chassot, Praroman (CH); Cècile Pasquier, Marly (CH); Guido Sauter, Thoerishaus (CH); Vèronique Buclin-Charrière, Morlon (CH)

(73) Assignee: Wella AG, Darmstadt (DE)

( * ) Notice: Subject to any disclaimer, the term of this patent is extended or adjusted under 35 U.S.C. 154(b) by 127 days.

(21) Appl. No.: 10/480,908

(22) PCT Filed: Feb. 20, 2003

(86) PCT No.: PCT/EP03/01699

§ 371 (c)(1),
(2), (4) Date: Dec. 15, 2003

(87) PCT Pub. No.: WO03/082823

PCT Pub. Date: Oct. 9, 2003

(65) Prior Publication Data

US 2004/0158936 A1 Aug. 19, 2004

(51) Int. Cl.
*A61K 7/13* (2006.01)
(52) U.S. Cl. ............... 8/405; 8/437; 8/462; 8/568; 8/582; 8/586; 8/673
(58) Field of Classification Search .............. 8/405, 8/437, 462, 568, 582, 586, 673
See application file for complete search history.

(56) References Cited

U.S. PATENT DOCUMENTS 4,031,088 A 6/1977 Ackerman
2002/0017218 A1 2/2002 Kurt et al.

FOREIGN PATENT DOCUMENTS

EP 1 160 291 12/2001
WO 01/68042 9/2001

OTHER PUBLICATIONS

STIC Search Report.*
Database CA Online Chemical Abstracts Service, Columbus, Ohio, US YLI-Kauhaluoma et al "Twisted. Alpha-Keto . . . " Database Accession No. 121:280443 XP002261682 CAS RN 5502-64-7 & Bioorganic & Medicinal Chemistry 1994, 2 (6), 521-8, ISSN 0968-0896.
Database CA Online, Chemical Abstracts Service, Columbus, Ohio, US; Shirai, M., et al:"Interaction Between Dyes and . . . " Retrieved Fromn Database Accession No. 98:107916 XP002261683 CAS RN 84890-26-6 & Makromolekulare Chemie 1983, 184(1), 153-63, ISSN 0025-116X.
Database CA Online Chemical Abstracts Service, Columbus, Ohio, US; Borek, F., et al: "Specificity of Delayed . . . " Retrieved From STN Database Accesseion No. 65:23705 XP002261686 CAS RN 5502-64-7 & Immunochemistry 1966, 3 (3), 247-50, ISSN 0019-2791.
Biffi, S., et al: "Glutaryl-7-Aca Acylase . . . " Journal of Molecular Catalysis B: Enzymatic, vol. 19-20, Dec. 2, 2002, pp. 135-141, XP002261681, ISSN 1381-1177.
Database CA Online Chemical Abstracts Service, Columbus, OH, US: Weissenfels, M., et al: "Reactions of Glutaric Acid . . . " Retrieved From Database Accession No. 96:142755 XP002261684 CAS RN 25901-27 & Zeitschrift Fuer Chemie 1982, 22 (1) 23-4, ISSN 0044-2402.
Cassebaum, H., et al: "Iodinated N . . . " Pharmazie, vol. 27, No. 6, 1972, pp. 391-395.
Database CA Online Chemical Abstracts Service Columbus, OH, US: Ozegowki et al:"Amino Acid . . . "Retrieved From STN Database Accession No. 59:35575 XP002261685 CAS RN 93819-29-5 & Journal Fuer Praktische Chemie (Leipzig 1963, 20, 178-86, ISSN 0021-8383.

* cited by examiner

*Primary Examiner*—Eisa Elhilo
(74) *Attorney, Agent, or Firm*—Michael J. Striker

(57) ABSTRACT

Pro-dyes of direct dyes having an enzymatically-labile functionality, e.g. glutaramide derivatives of direct dyes of formula (I) or their physiologically acceptable salts,

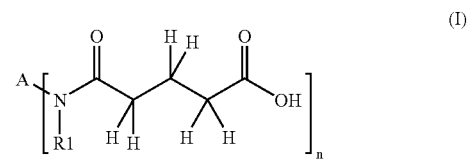

are described, as well as compositions for dyeing keratinous fibers containing these pro-dyes, as well as compositions for dyeing keratinous fibers containing a combination of at least one pro-dye and at least one enzyme capable of cleaving the glutaramide functionality in the pro-dye. A method for dyeing keratinous fibers with the aforementioned dyeing compositions is also described.

17 Claims, No Drawings

COMPOSITIONS AND METHODS FOR DYEING KERATINOUS FIBERS

The present invention relates to the use of pro-dyes, particularly glutaramide derivatives, combined with a suitable enzyme for dyeing keratinous fibers, in particular human keratin fibers such as hair, to the dye composition containing them and processes using these compositions.

BACKGROUND OF THE INVENTION

Methods for dyeing keratinous fibers such as hair have been widely sought. Dyeing involves contacting the material to be colored with a solution or formulation containing the dye substance. However, problems are encountered with certain dye substances. Some dye substances are insoluble in the dyeing solution or formulation. Problems also arise if the dye substance has an insufficient temperature stability to be stored for extended periods of time. In such cases, practical application of such a dye substance is difficult, even if the coloration properties are otherwise highly desirable.

The inventors have now discovered, surprisingly and unexpectedly that pro-dyes of direct dyes having an enzymatically-labile functionality, particularly the derivatives of direct dyes of formula (I) defined below, referred to herein as pro-dyes, can in presence of a suitable enzyme dye the keratinous fibers. The enzyme cleaves the enzymatically-labile functionality, e.g. the glutaramide functionality, liberating the direct dye, which then colors the fiber.

As used herein, "direct dye" means a chemical composition that is capable of dyeing or coloring a dye-susceptible material without further chemical modification. As used herein, "pro-dye" means a derivative of a direct dye with a enzymatically-labile functionality, and which is converted into a direct dye in the presence of a suitable enzyme that can catalyze a reaction with said enzymatically-labile functionality. As used herein, "enzymatically-labile functionality" means a chemical functional group that can be reacted, cleaved, or modified in the presence of a suitable enzyme, e.g. the glutaramide group.

DESCRIPTION OF THE INVENTION

Suitable pro-dyes that can serve as precursors for direct dyes containing one or more amine functional groups include any amide derivatives in which the amide can be hydrolyzed by an amidase, protease, peptidase, or other amide-hydrolyzing enzyme. Suitable pro-dyes include amide derivatives such as acetamides, propionamides, butyramides, benzamides, phenylacetamides, substituted phenylacetamides, succinamides, glutaramides, adipic acid amides, phthalamides, and the like. Other amides derivatives useful as pro-dyes in the practice of this invention include amides formed from amino acids that can be cleaved with a suitable protease, amidase, or peptidase. Amino acids from which pro-dye amides can be formed include both natural amino acids, such as those used as the building blocks of most proteins and non-naturally occurring amino acids. Examples of amino acids useful in the preparation of pro-dye amides with amine-containing dye substances and direct dyes include, but are not limited to leucine (cleaved, for example by leucine aminopeptidase); phenylalanine, tyrosine, or tryptophan (cleaved, for example, by chymostrypsin); lysine, arginine, or ornithine, cleaved, for example, by trypsin); aspartic acid, glutamic acid, or methionine (cleaved, for example by papain); alanine, valine, homoserine, and serine (cleaved, for example by subtlisin); proline and hydroxyproline (cleaved, for example by proline aminopeptidase); and many other examples. Non-naturally occurring amino acids that may be used and cleaved with suitable proteases and amidases include, but are not limited to phenylglycine, p-hydroxy-phenylglycine, 2-aminobutyric acid, 2-aminoadipic acid, and the like.

Suitable pro-dyes that can serve as precursors for direct dyes containing one or more hydroxy functional groups include any ester derivatives in which the ester can be hydrolyzed by an esterase, lipase, protease, peptidase, amidase, or other ester-hydrolyzing enzyme. Suitable pro-dyes include ester derivatives such as acetates, propionates, butyrates, benzoates, substituted benzoates, phenylacetates, substituted phenylacetates, succinates, glutarates, adipates, phthalates, palmitates, oleates, stearates, glycerates, gluconates, and the like. Ester derivatives of amino acids can also be used. In general, the same or similar enzymes used to hydrolyze amino acid amide derivatives can also be used to hydrolyze amino acid ester derivatives. Thus, phenylalanine, tyrosine, or tryptophan esters can be used and cleaved with, for example, chymostrypsin; lysine, arginine, or ornithine esters can be used and cleaved, for example, by trypsin; aspartic acid, glutamic acid, or methionine esters can be used and cleaved, for example by papain; alanine, valine, homoserine, and serine esters can be used and cleaved, for example by subtlisin; proline and hydroxyproline esters can be used and cleaved, for example by proline aminopeptidase. It will be evident to those skilled in the art that many other pro-dye derivatives with enzyme-cleavable groups and suitable enzymes exist, and that as the enzyme can be used a single enzyme or an enzyme mixture, and such broad application is explicitly contemplated as a part of this invention.

In a preferred embodiment, pro-dyes of direct dyes are formed, which are glutaramide derivatives of direct dyes according to formula (I) or their physiologically acceptable salts,

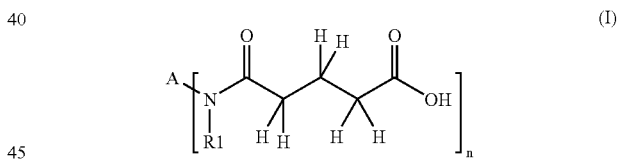

(I)

in which
R1 denotes hydrogen, a C1–C4-alkyl radical or a C1–C4-hydroxyalkyl radical,
n is 1,
A denotes a residue selected from the group consisting of
(i) nitrobenzenes of the formula (II),

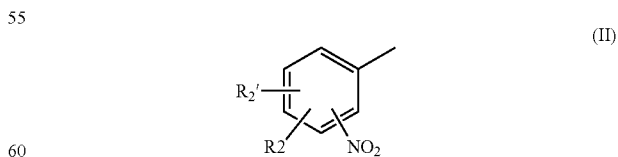

(II)

in which R2' denotes hydrogen and R2 denotes hydrogen, a halogen atom, a cyano group, a nitro group, a C1–C4-alkyl radical, a trifluoromethyl radical, a hydroxy group, a C1–C4-alkoxy radical, a C1–C4-hydroxyalkoxy radical, an amino group, a (C1–C4-alkyl)amino radical, a (C1–C4- hydroxy-alkyl)amino radical, a di(C1–C4-alkyl)amino radical, a (C1–C4-alkyl-(C1–C4-hydroxyalkyl)amino radical, a di(C1–C4-hydroxyalkyl)amino radical, a (C1–C4-alkyl)-(C1–C4-hydroxyalkyl)amino radical, an amino-(C1–C4-alkyl) radical, a —(C1–C4-alkyl)-NH—CO—NH2 group, a —COOH group, a —CONH2 group or a N-substituted phenyl—amino group, or R2' and R2 together form a —NH—(C1–C2-alkyl)-NH— bridge or a —NH—(C1–C2-alkyl)-O— bridge;

(ii) nitro-pyridines of the formula (III),

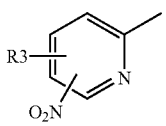

(III)

in which R3 denotes hydrogen, an amino group, a C1–C4-alkylamino radical or a (C1–C4-hydroxyalkyl)amino radical;

(iii) anthraquinones of the formula (IV),

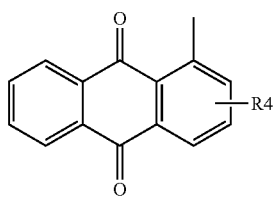

(IV)

in which R4 denotes hydrogen, an amino group, a C1–C4-alkylamino radical, a (C1–C4-hydroxyalkyl)amino radical, a —NH—(C1–C4-alkyl)-NH2 group, a hydroxy group or a C1–C4-alkoxy radical;

(iv) azo-dyes of the formula (V),

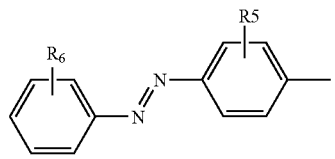

(V)

in which R5 denotes hydrogen, an amino group, a nitro group, a C1–C4-alkyl radical or a C1–C4-alkoxy radical, and R6 denotes hydrogen, a C1–C4-alkyl radical, a nitro group, a hydroxy group, a C1–C4-alkylamino radical, a (C1–C4-hydroxyalkyl)amino radical, a di(C1–C4-alkyl) amino radical, a di(C1–C4-hydroxyalkyl)amino radical or a tri(C1–C4-alkyl)-ammonium radical;

(v) azo-dyes of the formula (VI),

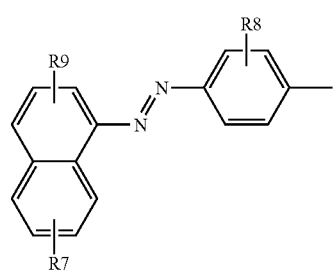

(VI)

in which R7 and R9 independently of each other denote hydrogen, a C1–C4-alkyl radical, a nitro group, a hydroxy group, a C1–C4-alkylamino radical, a (C1–C4-hydroxyalkyl)amino radical, a di(C1–C4-alkyl)amino radical, a di(C1–C4-hydroxyalkyl)amino radical or a tri(C1–C4-alkyl)-ammonium radical, and R8 denotes hydrogen, an amino group, a nitro group, a C1–C4-alkyl radical or a C1–C4-alkoxy radical;

(vi) azo-dyes of the formula (VII),

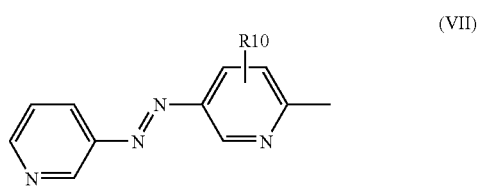

(VII)

in which R10 denotes hydrogen, an amino group, a nitro group, a C1–C4-alkyl radical or a C1–C4-alkoxy radical; and (vii) naphthoquinoneimine-dyes of the formula (VIII),

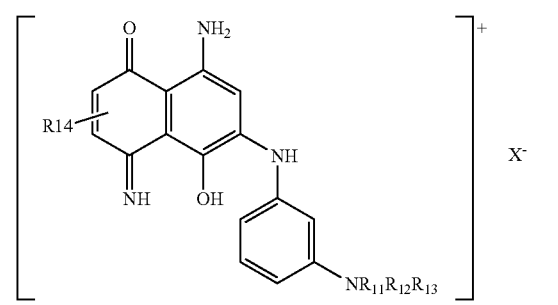

(VIII)

in which R11, R12 and R13 independently of each other denote hydrogen or a C1–C4-alkyl radical; R14 denotes a halogen atom, hydrogen or a C1–C4-alkyl radical; and $X^-$ denotes an anion.

A further object of the present invention are cosmetic compositions for dyeing keratin fibers, particularly human hairs, containing the above pro-dyes and particularly the glutaramide derivatives of formula (I).

In the practice of this invention, examples of direct dyes that are useful as the basis for the preparation of a pro-dye include nitroanilines, amino-nitrophenols, amino-nitropyridines, amino-anthraquinones, amino-azodyes, acidic dyes, basic dyes and the like.

Examples for suitable pro-dyes of formula (I) are monoglutaramide or di-glutaramide derivatives of the following direct dyes:

1-Amino-3-methyl-4-[(2-hydroxyethyl)amino]-6-nitrobenzene (HC Violet No. 1), 2-((4-Amino-2-nitrophenyl) amino)-5-dimethylamino-benzoic acid (HC Blue No. 13), 1-Amino-4-[(2-hydroxyethyl)amino]-2-nitrobenzene (HC Red No. 7), 2-Amino-4,6-dinitro-phenol, 1,4-Diamino-2-nitrobenzene (CI76070), 4-Amino-2-nitro-diphenylamine (HC Red No. 1), 1-Amino-4-[di(2-hydroxyethyl)amino]-2-nitrobenzene-hydrochloride (HC Red No. 13), 1-Amino-5-chloro-4-[(2-hydroxyethyl)amino]-2-nitrobenzene, 4-Amino-1-[(2-hydroxyethyl)amino]-2-nitrobenzene (HC Red No. 3), 1-Amino-4-((2,3-dihydroxypropyl)amino)-5-methyl-2-nitrobenzene, 1-Amino-4-(methylamino)-2-nitrobenzene, 4-Amino-2-nitro-1-((prop-2-en-1-yl)amino)-benzene, 4-Amino-3-nitrophenol, 1-Amino-5-chloro-4-[(2,3-dihydroxypropyl)amino]-2-nitrobenzene (HC Red No. 10), 2-[(4-Amino-2-nitrophenyl)amino]-benzoic acid, 2-Amino-6-chloro-4-nitrophenol-hydrochloride, 2,5-diamino-6-nitropyridine, 6-Amino-3-((2-hydroxyethyl)amino)-2-nitropyridine, 3-Amino-6-((2-hydroxyethyl)amino)-2-nitro-pyridine, 3-Amino-6-(ethylamino)-2-nitropyridine, 3-Amino-6-(methylamino)-2-nitropyridine, 7-Amino-3,4-dihydro-6-nitro-2H-1,4-benzoxazine (HC Red No. 14) 1,2-Diamino-4-nitrobenzene (CI76020), 1-Amino-2-[(2-hydroxyethyl)-amino]-5-nitrobenzene (HC Yellow No. 5), 2-Amino-3-nitrophenol, 1-Amino-2-methyl-6-nitrobenzene, 1-Amino-4-((2-aminoethyl)amino)-5-methyl-2-nitro-benzene, 1-Amino-4-hydroxy-9,10-anthraquinone (CI60710, Disperse Red 15), 1-[(3-Aminopropyl)amino] 4-methylamino-9,10-anthraquinone (HC Blue No. 8), 1-[(3-Aminopropyl)-amino]-9,10-anthraquinone (HC Red No. 8), 1,4-Diamino-2-methoxy-9,10-anthraquinone (CI62015, Disperse Red No. 11), 1,4-Diamino-9,10-anthraquinone (CI61100, Disperse Violet No. 1), 1-Amino-4-(methylamino)-9,10-anthraquinone (CI61105, Disperse Violet No. 4), 8-Amino-2-bromo-5-hydroxy-4-imino-6-[(3-(trimethylammonio)phenyl)-amino]-1(4H)-naphthalinone-chloride (C156059; Basic Blue No. 99), Tri(4-amino-3-methylphenyl)carbenium-chloride (C142520; Basic Violet No. 2), Di(4-aminophenyl)(4-amino-3-methylphenyl)carbenium-chloride (CI42510; Basic Violet No. 14), 1,3-Bis[(2,4-diamino-5-methylphenyl)azo]-3-methylbenzol (C121010; Basic Brown No. 4), 1-[(4-Amino-phenyl)azo]-7-(trimethylammonio)-2-naphthol-chloride (CI12250; Basic Brown No. 16), 3-[(4-Amino-2,5-dimethoxyphenyl)azo]-N,N,N-trimethyl-benzeneaminium-chloride (CI112605, Basic Orange No. 69), 1-[(4-Amino-2-nitrophenyl)azo]-7-(trimethylammonio)-2-naphthol-chloride (Basic Brown No. 17), 1-[(4-Amino-3-nitrophenyl)azo]-7-(trimethylammonio)-2-naphthol-chloride (CI12251; Basic Brown No. 17), 3,7-Diamino-2,8-dimethyl-5-phenyl-phenazinium-chloride (C150240; Basic Red No. 2), 1-[Di(2-hydroxyethyl)-amino]-4-[(4-nitrophenyl)azo]-benzene (Disperse Black No. 9), 4-[(4-Amino-phenyl)azo]-1-[di(2-hydroxyethyl)amino]-3-methylbenzene (HC Yellow No. 7) and 2,6-Diamino-3-((pyridin-3-yl)azo)pyridine.

Particularly preferred compounds of formula (I) are 5-[5-amino-6-nitro-2-(pyridinyl)amino]-5-oxopentanoic acid and 5-[(6-amino-5-(3-pyridinyl-diazenyl)-2-pyridinyl)amino]-5-oxopentanoic acid.

Advantages of dyeing keratin fibers with the above pro-dyes, particularly the glutaramide derivatives of formula (I), include the following:

1) Many direct dyes are highly insoluble in dyeing solutions, particularly aqueous dyeing solutions. The pro-dye can be constructed so as to have higher solubility in the dyeing solution, resulting in the ability to achieve higher effective concentrations of the dye, increased rates of dyeing, and deeper and more intense colors.

2) The use of pro-dyes provides the ability to vary the concentrations of the dye over a wider range, giving greater range of colors and hues.

3) The pro-dye can be constructed so as to have increased stability relative to the stability of the direct dye, enabling more facile formulation and increased shelf life.

Pro-dyes are designed so that the enzymatically-labile functionality (e.g. the glutaramide functionality) will, in the presence of a suitable enzyme, cause release of the desired direct dye. In a particularly preferred embodiment, the direct dye is converted into a pro-dye derivative that, upon enzyme-catalyzed hydrolysis, will release the desired direct dye. Nevertheless many pro-dyes of formula (I) are equally able to color the fiber without hydrolysis.

The ready-to-use dyeing composition preferably contains from about 0.01 to about 25 percent by weight of said pro-dye or compound of formula (I).

For optimizing the coloring result and achieving specific color effects, additional compounds from the group of direct-acting dyestuffs, for example acid dyes, basic dyes, aromatic nitro dyestuffs, azo dyestuffs, anthraquinone dyestuffs or triphenylmethane dyestuffs may be added, either alone or as a mixture thereof, to the coloring preparation according to the invention. Suitable nitro dyestuffs are, for example, picramic acid, 4-(2',3'-dihydroxy-propyl)-amino-3-nitro-trifluoro-methyl benzene, 4-N-ethyl-N-(2'-hydroxyethyl)amino-1-(2'-hydroxyethyl)-amino-2-nitrobenzene, 2-chloro-6-ethylamino-4-nitrophenol, 1-hydroxy-2-β-hydroxyethylamino-4,6-dinitrobenzene, 4-(2'-hydroxyethyl)-amino-3-nitro-chlorobenzene and 4-(2'-hydroxyethyl)-amino-3-nitro-methyl benzene.

Suitable azo dyestuffs are, for example, 1-(2'-methoxyphenylazo)-2-hydroxy-7-trimethyl-ammonium-naphthalene (Basic Red 76), 4-(4'-sulfo-1-phenylazo)-1-(4''-sulfophenyl)-3-carboxy-5-hydroxypyrazolone (Acid Yellow 23).

Suitable anthraquinone dyestuffs are, for example, 1-methylamino-4-(2'-hydroxyethyl)amino-anthraquinone (Disperse Blue 3), 1,4-bis(2',3'-dihydroxypropyl)amino-anthraquinone, 1-methylamino-4-(amino-n-propyltrimethyl-ammonium)-anthraquinone (Basic Blue 22), 1,4-bis-(2-hydroxyethyl)amino-5,8-dihydroxy-anthraquinone (Disperse Blue 7) and 1-methylamino-4-aminopropylamino-anthraquinone (HC Blue 8).

An example for triphenylmethane dyestuffs is [4-[[4-diethylamino]-phenyl][4-(ethylamino)-1-naphthyl]methylene]-2,5-cyclohexadiene-1-ylidene]-N-ethylethaneamine (Basic Blue 7).

The preferred amount of additional direct-acting dyestuffs to be used is from about 0.01% to about 5% by weight of the total dyeing composition. An especially preferred amount of additional direct-acting dyestuffs to be used is from about 0.1% to about 4% by weight of the total dyeing composition.

The dyeing composition may be prepared in various physical forms. For example, a solution, preferably an aqueous or aqueous-alcoholic solution can be used. Alternatively, the dyeing composition may be prepared as a cream, gel, emulsion, powder or solid with a granular consistency. The composition consists of a mixture of the dye components with, optionally, other cosmetic additives usual for such preparations.

Usual cosmetic additives are, for example, solvents, such as water, low aliphatic monohydroxy or polyhydroxy alcohols, their esters and ethers, for example alkanols, particularly with an alkyl chain comprising 1 to 4 carbon atoms, such as ethanol, n-propanol or isopropanol, butanol, isobutanol; bivalent or trivalent alcohols, particularly of the type having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerine, diethylene glycol, dipropylene glycol, polyalkylene glycols, such as triethylene glycol, polyethylene glycol, tripropylene glycol and polypropylene glycol; low alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol mono ethyl ether, triethylene glycol monomethyl ether or triethylene glycol mono ethyl ether; ketones and keto alcohols, especially such with 3 to 7 carbon atoms in their molecules, such as acetone, methyl ethyl ketone, diethyl ketone, methyl isobutyl ketone, methyl phenyl ketone, cyclopentanone, cyclohexanone and diacetone alcohol; ethers such as dibutyl ether, tetra-hydrofurane, dioxane or diisopropyl ether; esters such as ethyl formate, methyl formate, methyl acetate, ethyl acetate, propyl acetate, butyl acetate, phenyl acetate, ethylene glycol monoethyl ether acetate or acetic acid hydroxy ethyl ester; amids such as dimethyl formamide, dimethyl acetamide or N-methyl-pyrrolidone; as well as urea, tetramethyl urea and thiodiglycol; moreover, wetting agents or emulsifyers from the group of anionic, cationic, non-ionogenic, amphoteric or zwitterionic surface-active substances, such as fatty alcohol sulfates, alkyl-sulfonates, alkylbenzene sulfonates, alkyltrimethyl ammonium salts, alkylbetaines, α-olefin sulfonates, oxethylated fatty alcohols, oxethylated nonylphenols, fatty acid alkanolamines, oxethylated fatty acid esters, fatty alcohol polyglycol ether sulfates, alkylpolyglucosides; thickening agents, such as high fatty alcohols, starch, cellulose derivatives, vaseline, paraffin oil, fatty acids and other fatty components in emulsified form, water-soluble polymeric thickening agents, for instance natural rubbers, guar gum, xanthan gum, carob flour, pectine, dextrane, agar-agar, amylose, amylopectine, dextrine, clays or synthetic hydrocolloides, such as polyvinyl alcohol; also conditioning agents, such as lanolin derivatives, cholesterol, pantothenic acid, water-soluble cationic polymers, protein derivatives, pro-vitamins, vitamins, plant extracts, sugar and betaine; auxiliary agents, such as electrolytes, antioxidants, fatty amides, sequestrants, film-forming agents and preservatives.

The aforementioned cosmetic additives are used in the amounts usual for such purposes, for example, wetting agents and emulsifying agents in concentrations of about 0.5% to about 30% by weight, thickening agents of from about 0.1% to about 25% by weight, and conditioning agents in concentrations of from about 0.1% to about 5.0% by weight.

Although many of the pro-dyes (especially of formula (I)) are able to dye keratinous fibers without the addition of enzymes the compositions according to the invention preferably contain a combination of the pro-dye (particularly the glutaramide pro-dye of formula (I)) and an enzyme capable of reacting, cleaving, or modifying the enzymatically-labile functionality to form a direct dye.

The aforesaid pro-dye and enzyme components of the dyeing composition of this invention may be prepared, for example, as a solution, emulsion, a suspension or similar. In a preferred embodiment, the solution is an aqueous or aqueous-alcoholic solution. In other embodiments, the composition may be prepared as a cream, gel, emulsion, powder or as a solid of granular consistency. The composition preferably consists of, at a minimum, a mixture of the pro-dye and the enzyme.

In a particularly preferred embodiment, the pro-dye or compound of formula (I) and the enzyme are prepared as separate components (A) and (B), and the two components are combined just before use to form the ready-to-apply dyeing composition.

In another embodiment, the pro-dye or compound of formula (I) and the enzyme are combined and stored in an aqueous solution at a pH at which the enzyme and the pro-dye or compound of formula (I) are stable but at which the enzyme-catalyzed reaction does not take place. Before use the pH is adjusted into the range at which the enzyme is catalytically active to form the ready-to-apply dyeing composition.

The dyeing compositions according to this invention may be applied in various ways. For instance, the components (A) and (B) may be mixed prior to use and be spread on the fibers to be colored either immediately or after an incubation time of 15 to 45 minutes. The mixture is left on the material to be colored, such as hair, at about 15 to 50° C., for a time period of from about 1 minute to about 75 minutes, and more preferably of from about 25 minutes to about 40 minutes. The material is then rinsed with water and dried. In the case of hair coloring, after rinsing, the hair may be washed with a shampoo and/or subsequently be rinsed with a weak organic acid, such as citric acid, glycolic acid, lactic acid, malic acid, ascorbic acid or tartaric acid.

The ready-to-use dyeing composition has a pH-value of from about 4 to about 10.5, more preferably of from 6 to 10, most preferably of from 7.0 to 9.5.

The dyeing composition/dyeing method according to the present invention achieves (especially on human hair) color results with excellent fastness properties, especially with regard to light, shampooing and friction. Depending on the type and concentration of the pro-dyes or compounds of the general formula (I), a variety of different color shades can be obtained with the coloring preparation according to this invention. The high intensity and purity of the colors obtained with the preparation according to the invention are particularly noteworthy. In addition, the described coloring preparation also permits coloring grey and chemically undamaged hair without problems and obtaining a very good covering effect. The color results thus achieved are, irrespective of different hair structures, uniform and highly reproducible.

Due to their stability against oxidants the pro-dyes and especially the compounds of formula (I) can also be used in the presence of hydrogen peroxide.

The following examples should illustrate the subject matter of the present invention in detail, without limiting the broad concept of the invention or the claims appended hereinbelow.

EXAMPLES

A. Preparation of Pro-Dyes

Example 1

Preparation of 5-[5-amino-6-nitro-2-(pyridinyl) amino]-5-oxopentanoic acid (=glutaramide of 2,5-diamino-6-nitropyridine)

To a mixture of 3.08 g (20 mmol) of 2,5-diamino-6-nitropyridine and 0.36 g (3 mmol) of N,N-dimethylamino-pyridine in 120 ml of tetrahydrofurane, 5.7 g (50 mmol) of glutaric anhydride were added at room temperature. The mixture was stirred for 3 hours at room temperature and then refluxed for additional 3 hours. The mixture was then filtered, the solvent was evaporated and the crude product was dissolved in ethylacetate and extracted three times with a 1N sodium hydroxide solution. The combined aqueous extracts were acidified with conc. HCl at 0° C. A precipitate was formed, and filtration yielded an orange solid. The solid so obtained was washed with water. After drying 4.33 g (81% yield) of 5-[5-amino-6-nitro-2-pyridinyl)amino]-5-oxopentanoic acid were obtained.

Example 2

Preparation of 5-[(6-amino-5-(3-pyridinyldiazenyl)-2-pyridinyl)amino]-5-oxopentanoic acid (=glutaramide of 2,6-diamino-3-((pyridin-3-yl)azo)pyridine)

To a mixture of 3.21 g (15 mmol) of 2,6-diamino-3-((pyridin-3-yl)azo)pyridine and 0.27 g (2.2 mmol) of N,N-dimethylamino-pyridine in 100 ml of tetrahydrofurane, 4.27 g (37.5 mmol) of glutaric anhydride was added at room temperature. The mixture was refluxed for 16 hours. The mixture was then filtered, the solvent was evaporated and the crude product was dissolved in ethylacetate and extracted three times with a 1N sodium hydroxide solution. The combined aqueous extracts were acidified with conc. HCl at 0° C. A precipitate was formed, and filtration yielded an orange solid. The solid so obtained was washed with water. After drying the product was recristallised in methanol/water mixture and 1.9 g (40% yield) of 5-[(6-amino-5-(3-pyridinyldiazenyl)-2-pyridinyl)amino]-5-oxopentanoic acid were obtained.

Examples 3–45

Preparation of Glutaramides of Alternative Amine-containing Direct Dyes to Produce Pro-dyes Procedures analogous to those used in Example 1 or Example 2 can be repeated with minor modifications to produce mono-glutaramide or di-glutaramide pro-dyes from the following 43 amine-containing direct dyes:

3. 1-Amino-3-methyl-4-[(2-hydroxyethyl)amino]-6-nitrobenzene (HC Violet No. 1),
4. 2-((4-Amino-2-nitrophenyl)amino)-5-dimethylaminobenzoic acid (HC Blue No. 13),
5. 1-Amino-4-[(2-hydroxyethyl)amino]-2-nitrobenzene (HC Red No. 7),
6. 2-Amino-4,6-dinitro-phenol,
7. 1,4-Diamino-2-nitrobenzene (CI76070),
8. 4-Amino-2-nitrodiphenylamine (HC Red No. 1),
9. 1-Amino-4-[di(2-hydroxyethyl)amino]-2-nitrobenzene-hydrochloride (HC Red No. 13),
10. 1-Amino-5-chloro-4-[(2-hydroxyethyl)amino]-2-nitrobenzene,
11. 4-Amino-1-[(2-hydroxyethyl)amino]-2-nitrobenzene (HC Red No. 3),
12. 1-Amino-4-((2,3-dihydroxypropyl)amino)-5-methyl-2-nitrobenzene,
13. 1-Amino-4-(methylamino)-2-nitrobenzene,
14. 4-Amino-2-nitro-1-((prop-2-en-1-yl)amino)-benzene,
15. 4-Amino-3-nitrophenol,
16. 1-Amino-5-chloro-4-[(2,3-dihydroxypropyl)amino]-2-nitrobenzene (HC Red No. 10),
17. 2-((4-Amino-2-nitrophenyl)amino)-benzoic acid
18. 2-Amino-6-chloro-4-nitrophenol-hydrochloride,
19. 6-Amino-3-((2-hydroxyethyl)amino)-2-nitropyridine,
20. 3-Amino-6-((2-hydroxyethyl)amino)-2-nitropyridine,
21. 3-Amino-6-(ethylamino)-2-nitropyridine,
22. 3-Amino-6-(methylamino)-2-nitropyridine,
23. 7-Amino-3,4-dihydro-6-nitro-2H-1,4-benzoxazine (HC Red No. 14)
24. 1,2-Diamino-4-nitrobenzene (CI76020),
25. 1-Amino-2-[(2-hydroxyethyl)amino]-5-nitrobenzene (HC Yellow No. 5),
26. 2-Amino-3-nitrophenol,
27. 1-Amino-2-methyl-6-nitrobenzene,
28. 1-Amino-4-((2-aminoethyl)amino)-5-methyl-2-nitrobenzene,
29. 1-Amino-4-hydroxy-9,10-anthraquinone (CI60710, Disperse Red 15),
30. 1-[(3-Aminopropyl)amino]-4-methylamino-9,10-anthraquinone (HC Blue No. 8),
31. 1-[(3-Aminopropyl)amino]-9,10-anthraquinone (HC Red No. 8),
32. 1,4-Diamino-2-methoxy-9,10-anthraquinone (C162015, Disperse Red No. 11),
33. 1,4-Diamino-9,10-anthraquinone (CI61100, Disperse Violet No. 1),
34. 1-Amino-4-(methylamino)-9,10-anthraquinone (CI61105, Disperse Violet No. 4)
35. 8-Amino-2-bromo-5-hydroxy-4-imino-6-[(3-(trimethylammonio)phenyl)-amino]-1 (4H)-naphthalinone-chloride (CI56059; Basic Blue No. 99),
36. Tri(4-amino-3-methylphenyl)carbenium-chloride (C142520; Basic Violet No. 2),
37. Di(4-aminophenyl)(4-amino-3-methylphenyl)carbenium-chloride (CI42510; Basic Violet No. 14),
38. 1,3-Bis[(2,4-diamino-5-methylphenyl)azo]-3-methylbenzol (CI21010; Basic Brown No. 4),
39. 1-[(4-Aminophenyl)azo]-7-(trimethylammonio)-2-naphthol-chloride (CI12250; Basic Brown No. 16),
40. 3-[(4-Amino-2,5-dimethoxyphenyl)azo]-N,N,N-trimethylbenzeneaminium-chloride (CI112605, Basic Orange No. 69),
41. 1-[(4-Amino-2-nitrophenyl)azo]-7-(trimethylammonio)-2-naphthol-chlorid (Basic Brown No. 17),
42. 1-[(4-Amino-3-nitrophenyl)azo]-7-(trimethylammonio)-2-naphthol-chlorid (CI12251; Basic Brown No. 17),
43. 3,7-Diamino-2,8-dimethyl-5-phenylphenazinium-chloride (CI50240; Basic Red No. 2),
44. 1-[Di(2-hydroxyethyl)amino]-4-[(4-nitrophenyl)azo]-benzene (Disperse Black No. 9),
45. 4-[(4-Aminophenyl)azo]-1-[di(2-hydroxyethyl)amino]-3-methylbenzene (HC Yellow No. 7).

Example 46–83

Preparation of L-lysine Amides of Alternative Amine-containing Direct Dyes to Produce Pro-dyes Procedures analogous to those used in Example 1 or Example 2 can be repeated with minor modifications (using N,N-alpha,epsilon-di-t-BOC-L-lysine N-hydroxysuccinimidyl ester (Sigma Chemical Company, St. Louis, Mo.; product number B7019) in chloroform instead of glutaric anhydride in THF) to produce L-lysine amide pro-dyes from the following amine-containing direct dyes:

46. 1-Amino-4-[(2-hydroxyethyl)amino]-2-nitrobenzol (HC Red No. 7),
47. 2-Amino-4,6-dinitro-phenol,
48. 1,4-Diamino-2-nitrobenzol (CI76070),
49. 4-Amino-2-nitro-diphenylamin (HC Red No. 1),
50. 1-Amino-4-[di(2-hydroxyethyl)amino]-2-nitrobenzol-hydrochlorid (HC Red No. 13), 51. 1-Amino-5-chlor-4-[(2-hydroxyethyl)amino]-2-nitrobenzol,
52. 4-Amino-1-[(2-hydroxyethyl)amino]-2-nitrobenzol (HC Red No. 3),
53. 4-((2-Hydroxyethyl)methylamino)-1-(methylamino)-2-nitrobenzol,
54. 1-Amino-4-((2,3-dihydroxypropyl)amino)-5-methyl-2-nitrobenzol,
55. 1-Amino-4-(methylamino)-2-nitrobenzol,
56. 4-Amino-2-nitro-1-((prop-2-en-1-yl)amino)-benzol,
57. 4-Amino-3-nitrophenol,
58. 4-[(2-Hydroxyethyl)amino]-3-nitrophenol,
59. 1-Amino-5-chlor-4-[(2,3-dihydroxypropyl)amino]-2-nitrobenzol (HC Red No. 10),
60. 2-Amino-6-chlor-4-nitrophenol,
61. 6-Amino-3-((2-hydroxyethyl)amino)-2-nitropyridin,
62. 3-Amino-6-((2-hydroxyethyl)amino)-2-nitropyridin,
63. 3-Amino-6-(ethylamino)-2-nitropyridin,
64. 3-Amino-6-(methylamino)-2-nitropyridin,
65. 7-Amino-3,4-dihydro-6-nitro-2H-1,4-benzoxazin (HC Red No. 14)
66. 1,2-Diamino-4-nitrobenzol (CI76020),
67. 1-Amino-2-[(2-hydroxyethyl)amino]-5-nitrobenzol (HC Yellow No. 5),
68. 2-Amino-3-nitrophenol,
69. 1-Amino-2-methyl-6-nitrobenzol,
70. 1-Amino-4-((2-aminoethyl)amino)-5-methyl-2-nitrobenzol,
71. 1-Amino-4-hydroxy-9,10-anthrachinon (C160710, Disperse Red 15),
72. 1-[(3-Aminopropyl)amino]-4-methylamino-9,10-anthrachinon (HC Blue No. 8),
73. 1-[(3-Aminopropyl)amino]-9,10-anthrachinon (HC Red No. 8),
74. 1,4-Diamino-2-methoxy-9,10-anthrachinon (C162015, Disperse Red No. 11, Solvent Violet No. 26),
75. 1,4-Diamino-9,10-anthrachinon (CI61100, Disperse Violet No. 1),
76. 1-Amino-4-(methylamino)-9,10-anthrachinon (CI61105, Disperse Violet No. 4, Solvent Violet No. 12).
77. 8-Amino-2-brom-5-hydroxy-4-imino-6-[(3-(trimethylammonio)phenyl)-amino]-1(4H)-naphthalinon-chlorid (CI56059; Basic Blue No. 99),
78. Di(4-aminophenyl)(4-amino-3-methylphenyl)carbenium-chlorid (CI42510; Basic Violet No. 14),
79. 1-[(4-Aminophenyl)azo]-7-(trimethylammonio)-2-naphthol-chlorid (CI12250; Basic Brown No. 16),
80. 3-[(4-Amino-2,5-dimethoxyphenyl)azo]-N,N,N-trimethylbenzolaminium-chlorid (CI112605, Basic Orange No. 69),
81. 1-[(4-Amino-2-nitrophenyl)azo]-7-(trimethylammonio)-2-naphthol-chlorid (Basic Brown No. 17),
82. 1-[(4-Amino-3-nitrophenyl)azo]-7-(trimethylammonio)-2-naphthol-chlorid (CI12251; Basic Brown No. 17),
83. 3,7-Diamino-2,8-dimethyl-5-phenylphenazinium-chlorid (CI50240; Basic Red No. 2).

B. Enzymatic Generation of Direct Dye From a Pro-dye

Example 84

Enzymatic Generation of Direct Nitro-dye From a Pro-dye with an Immobilized Enzyme A solution of 5-[5-amino-6-nitro-2-(pyridinyl)amino]-5-oxopentanoic acid (according to example 1) was prepared at a concentration of 100 mM in aqueous 200 mM potassium phosphate buffer, and the pH was adjusted to 7.5 by the addition of 6 M sodium hydroxide solution. The pH-adjusted glutaramide solution was diluted 1:10 (final concentration of 10 mM) into a 200 mM potassium phosphate buffer solution, pH 7.5, containing a suspension of immobilized glutaryl acylase (BioCatalytics, Inc., Pasadena, Calif. USA; Product Number 1464213) added to achieve a catalytic activity of 104 units per milliliter. As a negative control, an identical reaction mixture was prepared without the immobilized glutaryl acylase. The reaction mixtures were mixed gently at 37° C. and the progress of the reaction was followed by thin layer chromatography (silica gel plates, eluted with ethylacetate; visualization by UV-light). Complete conversion of the 5-[5-amino-6-nitro-2-(pyridinyl)amino]-5-oxopentanoic acid to 2,5-diamino-6-nitropyridine was achieved within 24 hours. In the case of the control reaction without enzyme, no conversion of the mono-glutaramide of 2,5-diamino-6-nitropyridine was detected over a 24 hour period.

Example 85

Enzymatic Generation of Direct Nitro-dye from a Pro-dye with a Non-immobilized Enzyme A solution of 5-[5-amino-6-nitro-2-(pyridinyl)amino]-5-oxopentanoic acid (according to example 1) was prepared at a concentration of 100 mM in aqueous 200 mM potassium phosphate buffer, and the pH was adjusted to 7.5 by the addition of 6 M sodium hydroxide solution. The pH-adjusted glutaramide solution was diluted 1:10 (final concentration of 10 mM) into a 200 mM potassium phosphate buffer solution, pH 7.5, containing the non-immobilized glutaryl acylase (BioCatalytics, Inc., Pasadena, Calif. USA; Product Number 1479725) added to achieve a catalytic activity of 104 units per milliliter. As a negative control, an identical reaction mixture was prepared without the non-immobilized glutaryl acylase. The reaction mixtures were mixed gently at 37° C. and the progress of the reaction was followed by thin layer chromatography (silica gel plates, eluted with ethylacetate; visualization by UV-light). Complete conversion of the 5-[5-amino-6-nitro-2-(pyridinyl)amino]-5-oxopentanoic acid to 2,5-diamino-6-nitropyridine was achieved within 30 minutes. In the case of the control reaction without enzyme, no conversion of the mono-glutaramide of 2,5-diamino-6-nitropyridine was detected over a 24 hour period.

Example 86

Enzymatic Generation of a Direct Azo-dye from a Pro-dye with an Immobilized Enzyme A suspension of 5-[(6-amino-5-(3-pyridinyldiazenyl)-2-pyridinyl)amino]-5-oxopentanoic acid (according to example 2) was prepared at a concentration of 100 mM in aqueous 200 mM potassium phosphate buffer, and the pH was adjusted to 7.5 by the addition of 6 M sodium hydroxide solution. The pH-adjusted glutaramide solution was diluted 1:10 (final concentration of 10 mM) into a 200 mM potassium phosphate buffer solution, pH 7.5, containing a suspension of immobilized glutaryl acylase (BioCatalytics, Inc., Pasadena, Calif. USA; Product Number 1464213) added to achieve a catalytic activity of 104 units per milliliter. As a negative control, an identical reaction mixture was prepared without the immobilized glutaryl acylase. The reaction mixtures were mixed gently at 37° C. and the progress of the reaction was followed by thin layer chromatography (silica gel plates, eluted with ethylacetate; visualization by UV-light). Complete conversion of the 5-[(6-amino-5-(3-pyridinyldiazenyl)-2-pyridinyl)amino]-5-oxopentanoic acid to 2,6-diamino-3-((pyridin-3-yl)azo) pyridine was achieved within 24 hours. In the case of the control reaction without enzyme, no conversion of the mono-glutaramide of 2,6-diamino-3-((pyridin-3-yl)azo)pyridine was detected over a 24 hour period.

Example 87

Enzymatic Generation of a Direct Azo-dye from a Pro-dye with an Immobilized Enzyme in the Presence of a Co-solvent A suspension of 5-[(6-amino-5-(3-pyridinyldiazenyl)-2-pyridinyl)amino]-5-oxopentanoic acid (according to example 2) was prepared by the addition of 3.28 mg per milliliter in aqueous 200 mM potassium phosphate buffer, pH 7.5, containing 20 vol % dimethylsulfoxide. Immobilized glutaryl acylase (BioCatalytics, Inc., Pasadena, Calif. USA; Product Number 1464213) was added to achieve a catalytic activity of 104 units per milliliter. As a negative control, an identical reaction mixture was prepared without the immobilized glutaryl acylase. The reaction mixtures were mixed gently at 37° C. and the progress of the reaction was followed by thin layer chromatography (silica gel plates, eluted with ethylacetate; visualization by UV-light). Complete conversion of the 5-[(6-amino-5-(3-pyridinyldiazenyl)-2-pyridinyl)amino]-5-oxopentanoic acid to 2,6-diamino-3-((pyridin-3-yl)azo)pyridine was achieved within 24 hours. In the case of the control reaction without enzyme, no conversion of the mono-glutaramide of 2,6-diamino-3-((pyridin-3-yl)azo)pyridine was detected over a 24 hour period.

Example 88

Enzymatic Generation of a Direct Azo-dye from a Pro-dye with a Non-immobilized Enzyme A suspension of 5-[(6-amino-5-(3-pyridinyldiazenyl)-2-pyridinyl)amino]-5-oxopentanoic acid (according to example 2) was prepared at a concentration of 100 mM in aqueous 200 mM potassium phosphate buffer, and the pH was adjusted to 7.5 by the addition of 6 M sodium hydroxide solution. The pH-adjusted glutaramide solution was diluted 1:10 (final concentration of 10 mM) into a 200 mM potassium phosphate buffer solution, pH 7.5, containing the non-immobilized glutaryl acylase (BioCatalytics, Inc., Pasadena, Calif. USA; Product Number 1479725) added to achieve a catalytic activity of 104 units per milliliter. As a negative control, an identical reaction mixture was prepared without the non-immobilized glutaryl acylase. The reaction mixtures were mixed gently at 37° C. and the progress of the reaction was followed by thin layer chromatography (silica gel plates, eluted with ethylacetate; visualization by UV light). Complete conversion of the 5-[5-amino-6-nitro-2-(pyridinyl)-amino]-5-oxopentanoic acid to 2,5-diamino-6-nitropyridine was achieved within 30 minutes. In the case of the control reaction without enzyme, no conversion of the mono-glutaramide of 2,5-diamino-6-nitropyridine was detected over a 24 hour period.

C. Enzymatic Dyeing With Pro-dye

Example 89

Dyeing Using a Pro-dye of a Direct Nitro-dye

Composition (A):

| | |
|---|---|
| 10 mmoles | 5-[5-amino-6-nitro-2-(pyridinyl)amino]-5-oxopentanoic acid (according to example 1) |
| 100 ml | 1 M potassium phosphate, pH 7.5 |
| 900 ml | water |

Composition (B):

| | |
|---|---|
| 1 g | non-immobilized glutaryl acylase (BioCatalytics, Inc., Pasadena, CA USA; Product number 1479725) |

1 gram (approximately 5000 units) of glutaryl acylase (BioCatalytics, Inc., Pasadena, Calif. USA; Product number 1479725) is added to fifty milliliters of composition (A), and the ingredients are mixed to form a dyeing solution. Bleached hair is treated with the dyeing solution at 37° C. for 30 minutes. At the end of this time, the hair shock is rinsed under cold running tap water, and dried. The hair is dyed a deep orange color.

Example 90

Dyeing Using a Pro-dye of a Direct Azo-dye

Composition (A):

| | |
|---|---|
| 10 mmoles | 5-[(6-amino-5-(3-pyridinyldiazenyl)-2-pyridinyl)amino]-5-oxopentanoic acid (according to example 2) |
| 100 ml | 1 M potassium phosphate, pH 7.5 |
| 900 ml | water |

Composition (B):

| | |
|---|---|
| 1 g | non-immobilized glutaryl acylase (BioCatalytics, Inc., Pasadena, CA USA; Product number 1479725) |

1 gram (approximately 500 units) of glutaryl acylase (BioCatalytics, Inc., Pasadena, Calif. USA; Product number 1479725) is added to fifty milliliters of composition (A), and the ingredients are mixed to form a dyeing solution. Bleached hair is treated with the dyeing solution at 37° C. for 30 minutes. At the end of this time, the hair shock is rinsed under cold running tap water, and dried. The hair is dyed a deep orange color.

Example 91

Dyeing Using a Pro-dye of a Direct Nitrobenzene Dye

Composition (A):

| 10 mmoles | glutaramide of 1-amino-3-methyl-4-[(2-hydroxyethyl)-amino]-6-nitrobenzene (HC Violet No. 1) |
|---|---|
| 100 ml | 1 M potassium phosphate, pH = 7.0 |
| 900 ml | water |

Composition (B):

| 1 g | glutaryl acylase (BioCatalytics, Inc., Pasadena, CA USA; Product number 1479725) |
|---|---|

To fifty milliliters of composition (A) is added 50 milligrams (=approximately 250 units) of composition (B), and the ingredients are mixed to form a dyeing solution. A shock of bleached hair (10 grams) is submerged in the dyeing solution. The dyeing solution containing the submerged hair is agitated slowly by orbital shaking at 37° C. for 30 minutes. At the end of this time, the hair is removed, rinsed under cold running tap water, and dried in air by placement on an absorbent paper towel. The hair is dyed a deep violet color.

Example 92

Dyeing Using a Pro-dye of a Direct Nitrobenzene Dye

Composition (A):

| 10 mmoles | glutaramide of 1-amino-4-[(2-hydroxyethyl)amino]-2-nitrobenzene (HC Red No. 7) |
|---|---|
| 100 ml | 1 M potassium phosphate, pH = 7.0 |
| 900 ml | water |

Composition (B):

| 1 g | glutaryl acylase (BioCatalytics, Inc., Pasadena, CA USA; Product number 1479725) |
|---|---|

To fifty milliliters of composition (A) is added 50 milligrams (=approximately 250 units) of composition (B), and the ingredients are mixed to form a dyeing solution. The dyeing is carried out as in Example 91.

The hair is dyed a deep red color.

Example 93

Dyeing Using a Pro-dye of a Direct Nitro Dye

Composition (A):

| 10 mmoles | glutaramide of 4-amino-2-nitro-diphenylamine (HC Red No. 1) |
|---|---|
| 100 ml | 1 M potassium phosphate, pH = 7.0 |
| 900 ml | water |

Composition (B):

| 1 g | glutaryl acylase (BioCatalytics, Inc., Pasadena, CA USA; Product number 1479725) |
|---|---|

To fifty milliliters of composition (A) is added 50 milligrams (=approximately 250 units) of composition (B), and the ingredients are mixed to form a dyeing solution. The dyeing is carried out as in Example 91.

The hair is dyed a deep red color.

Example 94

Dyeing Using a Pro-dye of a Direct Nitrobenzene Dye

Composition (A):

| 10 mmoles | glutaramide of 1-amino-2-methyl-6-nitrobenzene |
|---|---|
| 100 ml | 1 M potassium phosphate, pH = 7.0 |
| 900 ml | water |

Composition (B):

| 1 g | glutaryl acylase (BioCatalytics, Inc., Pasadena, CA USA; Product number 1479725) |
|---|---|

To fifty milliliters of composition (A) is added 50 milligrams (=approximately 250 units) of composition (B), and the ingredients are mixed to form a dyeing solution. The dyeing is carried out as in Example 91.

The hair is dyed a deep yellow color.

Example 95

Dyeing Using a Pro-dye of a Direct Quinone Dye

Composition (A):

| 10 mmoles | glutaramide of 1-amino-4-hydroxy-9,10-anthraquinone (CI60710, Disperse Red 15) |
|---|---|
| 100 ml | 1 M potassium phosphate, pH = 7.0 |
| 900 ml | water |

Composition (B):

| | |
|---|---|
| 1 g | glutaryl acylase (BioCatalytics, Inc., Pasadena, CA USA; Product number 1479725) |

To fifty milliliters of composition (A) is added 50 milligrams (=approximately 250 units) of composition (B), and the ingredients are mixed to form a dyeing solution. The dyeing is carried out as in Example 91.

The hair is dyed a deep red color.

Example 96

Dyeing Using a Phenylacetamide Pro-dye of a Direct Nitrobenzene Dye

Composition (A):

| | |
|---|---|
| 10 mmoles | phenylacetamide of 1-amino-3-methyl-4-[(2-hydroxyethyl)-amino]-6-nitrobenzene (HC Violet No. 1) |
| 100 ml | 1 M potassium phosphate, pH = 7.0 |
| 900 ml | water |

Composition (B):

| | |
|---|---|
| 1 g | penicillin amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep violet color.

Example 97

Dyeing Using a Phenylacetamide Pro-dye of a Direct Nitrobenzene Dye

Composition (A):

| | |
|---|---|
| 10 mmoles | phenylacetamide of 1-amino-4-[(2-hydroxyethyl)amino]-2-nitrobenzene (HC Red No. 7) |
| 100 ml | 1 M potassium phosphate, pH = 7.0 |
| 900 ml | water |

Composition (B):

| | |
|---|---|
| 1 g | penicillin amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep red color.

Example 98

Dyeing Using a Phenylacetamide Pro-dye of a Direct Nitro Dye

Composition (A):

| | |
|---|---|
| 10 mmoles | phenylacetamide of 4-amino-2-nitro-diphenylamine (HC Red No. 1) |
| 100 ml | 1 M potassium phosphate, pH = 7.0 |
| 900 ml | water |

Composition (B):

| | |
|---|---|
| 1 g | penicillin amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep red color.

Example 99

Dyeing Using a Phenylacetamide Pro-dye of a Direct Nitrobenzene Dye

Composition (A):

| | |
|---|---|
| 10 mmoles | phenylacetamide of 1-amino-2-methyl-6-nitrobenzene |
| 100 ml | 1 M potassium phosphate, pH = 7.0 |
| 900 ml | water |

Composition (B):

| | |
|---|---|
| 1 g | penicillin amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep yellow color.

Example 100

Dyeing Using a Phenylacetamide Pro-dye of a Direct Quinone Dye

Composition (A):

| | |
|---|---|
| 10 mmoles | phenylacetamide of 1-amino-4-hydroxy-9,10-anthraquinone (Cl60710, Disperse Red 15) |
| 100 ml | 1 M potassium phosphate, pH = 7.0 |
| 900 ml | water |

Composition (B):

| | |
|---|---|
| 1 g | penicillin amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep red color.

Example 101

Dyeing Using a Leucine Amide Pro-dye of a Direct Quinone Dye

Composition (A):

| | |
|---|---|
| 10 mmoles | L-leucinamide of 1-amino-4-hydroxy-9,10-anthraquinone (Cl60710, Disperse Red 15) |
| 1 M | potassium phosphate, pH = 7.0 |
| 900 ml | water |

Composition (B):

| | |
|---|---|
| 1 g | L-leucine amidase (BioCatalytics, Inc., Pasadena, CA USA; Product number 1290959) |

To fifty milliliters of composition (A) is added 50 milligrams (=approximately 500–1000 units) of composition (B), and the ingredients are mixed to form a dyeing solution. The dyeing is carried out as in Example 91.

The hair is dyed a deep red color.

Example 102

Dyeing Using an Aspartic Acid Amide Pro-dye of a Direct Quinone Dye

Composition (A):

| | |
|---|---|
| 10 mmoles | L-aspartic acid β-amide of 1-amino-4-hydroxy-9,10-anthraquinone (Cl60710, Disperse Red 15) |
| 100 ml | 1 M potassium phosphate, pH = 7.0 |
| 900 ml | water |

Composition (B):

| | |
|---|---|
| 1 g | papain (Sigma Chemical Co., St. Louis, MO USA) |

To fifty milliliters of composition (A) is added 50 milligrams (=approximately 250 units) of composition (B), and the ingredients are mixed to form a dyeing solution. The dyeing is carried out as in Example 91.

The hair is dyed a deep red color.

D. Dyeing Using a Pro-dye Without Any Enzyme

Example 103

Dyeing Using a Pro-dye of a Direct Nitro-dye

Dyeing Preparation

| | |
|---|---|
| 2.5 mmoles | 5-[5-amino-6-nitro-2-(pyridinyl)amino]-5-oxopentanoic acid (according to example 1) |
| 5.0 g | ethanol |
| 4.0 g | decyl-polyglucoside, 50% aqueous solution (Plantacare 2000, Cognis/DE) |
| 0.2 g | ethylenediaminetetraacetic acid disodium salt dihydrate |
| ad 100.0 g | water |

The ingredients are mixed together and the pH is adjusted with ammoniac or citric acid between 4 and 10 if needed. The dyeing preparation is applied to a shock of bleached buffalo hair for 30 minutes at 40° C. At the end of this time, the buffalo hair shock is rinsed under cold running tap water and dried.

The buffalo hair shock is dyed a deep golden yellow color.

Example 104

Dyeing Using a Pro-dye of a Direct Azo-dye

Dyeing Preparation

| | |
|---|---|
| 2.5 mmoles | 5-[(6-amino-5-(3-pyridinyldiazenyl)-2-pyridinyl)amino]-5-oxopentanoic acid (according to example 2) |
| 5.0 g | ethanol |
| 4.0 g | decyl-polyglucoside, 50% aqueous solution (Plantacare 2000, Cognis/DE) |

| | |
|---|---|
| 0.2 g | ethylenediaminetetraacetic acid disodium salt dihydrate |
| ad 100.0 g | water |

The ingredients are mixed together and the pH is adjusted with ammoniac or citric acid between 4 and 10 if needed. The dyeing preparation is applied to a shock of bleached buffalo hair for 30 minutes at 40° C. At the end of this time, the buffalo hair shock is rinsed under cold running tap water and dried.

The buffalo hair shock is dyed a deep golden yellow color.

All percentages given herein are percentages by weight, unless otherwise indicated.

The invention claimed is:

1. A pro-dye of a direct dye, wherein said pro-dye has an enzymatically-labile ester group and said enzymatically-labile ester group is hydrolysable by an esterase, lipase, protease, peptidase, amidase or another ester-hydrolyzing enzyme.

2. The pro-dye as defined in claim 1, wherein the pro-dye containing the enzymatically-labile ester group is a derivative of the direct dye and said derivative is selected from the group consisting of acetates, propionates, butyrates, benzoates, substituted benzoates, phenylacetates. substituted phenylacetates, succinates, glutarates, adipates, phthalates. palmitates, oleates, stearates, glycerates, gluconates, an ester derivative of phenylalanine, en ester derivative of tyrosine, an ester derivative of tryptophan. an ester derivative of lysine, an ester derivative of arginine, an ester derivative of ornithine, an ester derivative of aspartic acid, an ester derivative of glutamic acid, an ester derivative of methionine, an ester derivative of alanine, an ester derivative of valine, an ester derivative of homoserine, an ester derivative of serine, an ester derivative of proline and en ester derivative of hydroxyproline.

3. A pro-dye consisting of a glutaramide derivative of a direct dye, wherein said glutaramide derivative is a compound of formula (I), or a physiologically acceptable salt thereof:

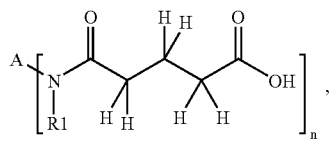
(1)

in which R1 denotes a hydrogen atom, a C1–C4-alkyl radical or a C1–C4-hydroxyalkyl radical;

n is 1;

and wherein A denotes a residue selected from the group consisting of;

(i) nitrobenzenes of the formula (II),

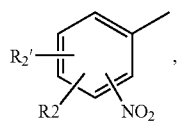
(II)

in which R2' denotes hydrogen and R2 denotes a halogen atom, a cyano group, a nitro group, a C1–C4-alkyl radical, a trifluoromethyl radical, a hydroxy group, a C1–C4-alkoxy radical, a C1–C4-hydroxyalkoxy radical, an amino group, a (C1–C4-alkyl)amino radical, a (C1–C4-hydroxyalkyl)amino radical, a di(C1–C4-alkyl)amino radical, a (C1–C4-alkyl)-(C1-C4-hydroxyalkyl)amino radical, a di(C1–C4-hydroxyalkyl)amino radical, a (C1–C4-alkyl)-(C1–C4-hydroxyalkyl)amino radical, an amino-(C1–C4-alkyl) radical, a -(C1–C4-alkyl)-NH—CO—NH2 group, a —COOH group, a —CONH2 group or a N-substituted phenylamino group, or R2' and R2 together form a —NH—(C1–C2-alkyl)-NH— bridge or a —NH—(C1–C2-alkyl)-O— bridge;

(ii) nitro-pyridines of the formula (III),

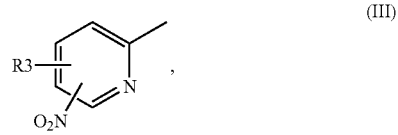
(III)

in which R3 denotes hydrogen, an amino group, a C1–C4-alkylamino radical or a (C1–C4-hydroxyalkyl)amino radical;

(iii) anthraquinones of the formula (IV),

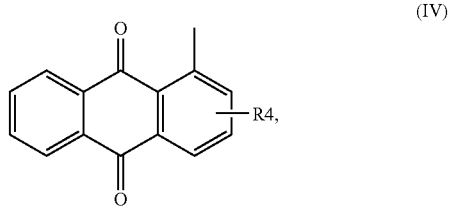
(IV)

in which R4 denotes hydrogen, an amino group, a C1–C4-alkylamino radical, a (C1–C4-hydroxyalkyl)amino radical, a —NH—(C1–C4-alkyl)-NH2 group, a hydroxy group or a C1–C4-alkoxy radical;

(iv) azo-dyes of the formula (V),

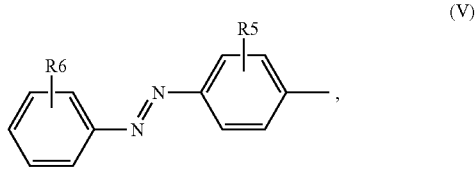
(V)

in which R5 denotes hydrogen, an amino group, a nitro group, a C1–C4-alkyl radical or a C1–C4-alkoxy radical, and R6 denotes hydrogen, a C1–C4-alkyl radical, a nitro group, a hydroxy group, a C1–C4-alkylamino radical, a (C1–C4-hydroxyalkyl)amino radical, a di(C1–C4-alkyl) amino radical, a di(C1–C4-hydroxyalkyl )amino radical or a tri(C1–C4-alkyl)-ammonium radical; with the proviso that R5 and R6 are not simultaneously hydrogen;

(v) azo-dyes of the formula (VI),

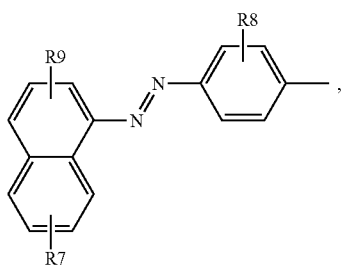

in which R7 and R9 independently of each other denote hydrogen, a C1–C4-alkyl radical, a nitro group, a hydroxy group, a C1–C4-alkylamino radical, a (C1–C4-hydroxyalkyl)amino radical, a di(C1–C4-alkyl)amino radical, a di(C1–C4-hydroxyalkyl)amino radical or a tri(C1–C4-alkyl)-ammonium radical, and R8 denotes hydrogen, an amino group, a nitro group, a C1–C4-alkyl radical or a C1–C4-alkoxy radical;

(vi) Azo-dyes of the formula (VII),

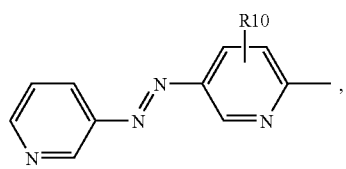

in which R10 denotes hydrogen, an amino group a nitro group, a C1–C4-alkyl radical or a C1–C4-alkoxy radical; and (vii) naphthoquinoneimine-dyes of the formula (VIII),

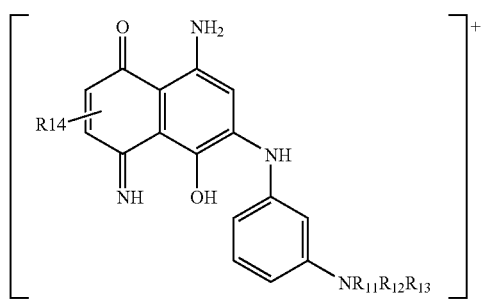

in which R11, R12 and R13, independently of each other, denote hydrogen or a C1–C4-alkyl radical; R14 denotes a halogen atom, hydrogen or a C1–C4-alkyl radical; and X⁻ denotes an anion.

4. The compound as define in claim 3, wherein said compound of formula (I) is selected from the group consisting of 5-[5-amino-6-nitro-2-(pyridinyl)amino]-5oxopentanoic acid and 5-[(6-amino-5-(3-pyridinyl-diazenyl)-2-pyridinyl)amino]-5-oxopentanoic acid.

5. A composition for coloring keratin fibers, said composition containing at least one pro-dye having an enzymatically-labile functionality and at least one enzyme capable of cleaving said enzymatically-labile functionality.

6. The composition as defined in claim 5, wherein said at least one pro-dye is a glutaramide derivative of a direct dye and said glutaramide derivative is a compound of formula (I), or a physiologically acceptable salt thereof:

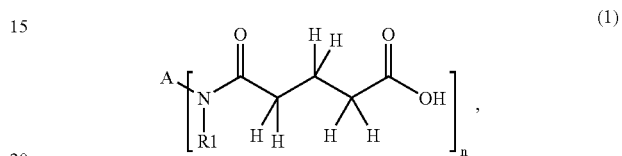

in which R1 denotes a hydrogen atom, a C1–C4-alkyl radical or a C1–C4-hydroxyalkyl radical;

n is 1;

and wherein A denotes a residue selected from the group consisting of:

(i) nitrobenzenes of the formula (II),

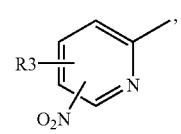

in which R2' denotes hydrogen and R2 denotes hydrogen, a halogen atom, a cyano group, a nitro group, a C1–C4-alkyl radical, a trifluoromethyl radical, a hydroxy group, a C1–C4-alkoxy radical, a C1–C4-hydroxyalkoxy radical, an amino group, a (C1–C4-alkyl)amino radical, a (C1–C4-hydroxy-alkyl)amino radical, a di(C1–C4-alkyl)amino radical, a (C1–C4-alkyl-(C1–C4-hydroxy-alkyl)amino radical, a di(C1–C4-hydroxyalkyl)amino radical, a (C1–C4-alkyl)-(C1–C4-hydroxyalkyl)amino radical, an amino-(C1–C4-alkyl) radical, a -(C1–C4-alkyl)-NH—CO—NH2 group, a —COOH group, a CONH2 group or a N-substituted phenylamino group, or R2' and R2 together form a NH—(C1–C2-alkyl)-NH— bridge or a —NH—(C1–C2-alkyl)-O— bridge;

(ii) nitropyridines of the formula (III),

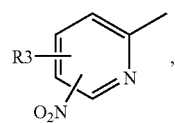

in which R3 denotes hydrogen, an amino group, a C1–C4-alkylamino radical or a (C1–C4-hydroxyalkyl)amino radical;

(iii) anthraquinones of the formula (IV),

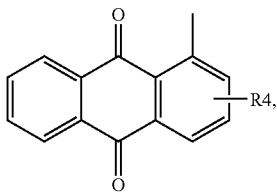
(IV)

in which R4 denotes hydrogen, an amino group, a C1–C4-alkylamino radical, a (C1–C4-hydroxyalkyl)amino radical, a —NH—(C1–C4-alkyl )-NH2 group, a hydroxy group or a C1–C4-alkoxy radical;

(iv) azo-dyes of the formula (V),

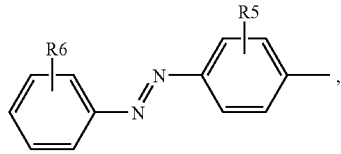
(V)

in which R5 denotes hydrogen, an amino group, a nitro group, a C1–C4-alkyl radical or a C1–C4-alkoxy radical, and R6 denotes hydrogen) a C1–C4-alkyl radical, a nitro group, a hydroxy group, a C1–C4-alkylamino radical, a (C1–C4-hydroxyalkyl)amino radical, a di(C1–C4-alkyl) amino radical, a di(C1–C4-hydroxy-alkyl)amino radical or a tri(C1–C4-alkyl)-ammonium radical;

(v) azo-dyes of the formula (VI),

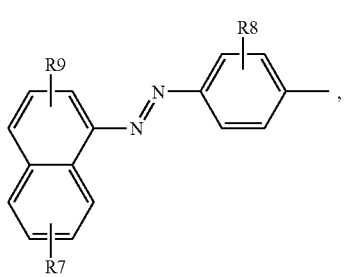
(VI)

in which R7 and R9 independently of each other denote hydrogen, a C1–C4-alkyl radical, a nitro group, a hydroxy group, a C1–C4-alkylamino radical, a (C1–C4-hydroxyalkyl)amino radical, a di(C1–C4-alkyl)amino radical, a di(C1–C4-hydroxyalkyl)amino radical or a tri(C1–C4-alkyl)-ammonium radical, and R8 denotes hydrogen, an amino group, a nitro group, a C1–C4-alkyl radical or a C1–C4-alkoxy radical;

(vi) azo-dyes of the formula (VII),

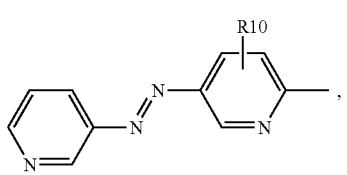
(VII)

In which R10 denotes hydrogen, an amino group, a nitro group, a C1–C4-alkyl radical or a C1–C4-alkoxy radical; and (vii) naphthoquinoneimine-dyes of the formula (VIII),

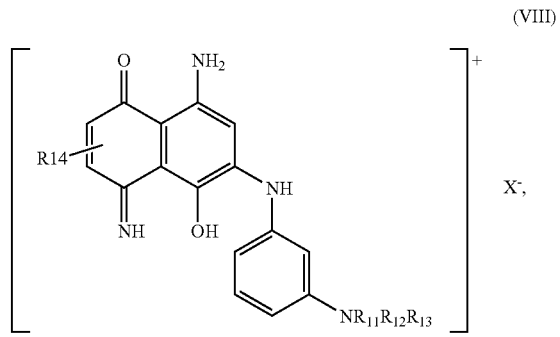
(VIII)

in which R11, R12 and R13, independently of each other, denote hydrogen or a C1–C4-alkyl radical; R14 denotes a halogen atom, hydrogen or a C1–C4-alkyl radical; and $X^-$ denotes an anion.

7. The composition as defined in claim 6, wherein said enzymatically-labile functionality is an enzymatically-labile ester or amide group in the at least one pro-dye.

8. The composition as defined in claim 7, wherein said at least one enzyme is selected from the group consisting of proteases, peptidases, amidases, esterases, lipases and acylases.

9. The composition as defined in claim 8, wherein said at least one enzyme is glutaryl acylase.

10. The composition as defined in claim 5, containing from 0.01 to 25 percent by weight of said at least one pro-dye.

11. The composition as defined in claim 5, further comprising at least one further direct-acting dyestuff, and wherein said at least one further direct-acting dyestuff is selected from the group consisting of acid dyes, basic dyes, aromatic nitro dyestuffs, azo dyestuffs, anthraquinone dyestuffs and triphenylmethane dyestuffs, or is a mixture thereof.

12. The composition as defined in claim 11, wherein said at least one further direct-acting dyestuff is contained in a total amount of from 0.01 to 5 percent by weight.

13. A composition for coloring keratin fibers in the form of a two-component kit, wherein said two-component kit consists of:
a component (A) comprising a pro-dye-containing composition, said pro-dye-containing composition containing at least one pro-dye and having an enzymatically-labile functionality; and
a component (B) comprising an enzyme-containing composition, said enzyme-containing composition containing at least one enzyme capable of cleaving the enzymatically-labile functionality of said at least one pro-dye.

14. A composition for coloring keratin fibers in the form of a two-component kit, wherein said two-component kit consists of:
a component (A) comprising a first composition, said first composition containing at least one pro-dye and at least one enzyme, wherein said at least one pro-dye has an enzymatically-labile functionality and said at least one enzyme is capable of cleaving the enzymatically-labile functionality of the at least one pro-dye, and wherein said first composition has a pH at which said at least one enzyme is stable but not active; and a component (B) comprising a second composition, said second composition containing a pH-adjuster capable of adjusting a pH of said first composition into a pH range in which the at feast one enzyme is active.

15. The composition as defined in claim 5, having a pH of from 4 to 10.5.

16. The composition as defined in claim 5, consisting of a hair dye composition.

17. A method of coloring keratin fibers, wherein said method comprises the steps of:
   a) providing a composition for coloring keratin fibers, said composition containing at least one pro-dye having an enzymatically-labile functionality and at least one enzyme capable of cleaving said enzymatically-labile functionality;
   b) applying said composition prepared in step a) to the keratin fibers to be colored; and
   c) after a development time of 10 to 45 minutes after the applying of step b), rinsing the keratin fibers with water and then drying.

* * * * *